United States Patent
Ruland et al.

(10) Patent No.: US 7,371,716 B2
(45) Date of Patent: *May 13, 2008

(54) C$_{10}$-ALKANOLALKOXYLATE MIXTURES AND THE USE THEREOF

(75) Inventors: Alfred Ruland, Schriesheim (DE);
Martin Scholtissek, Wachenheim (DE);
Juergen Tropsch, Roemerberg (DE);
Roland Boehn, Fussgoenheim (DE);
Claus Hackmann, Kirchheim (DE);
Christian Wulff, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 363 days.

This patent is subject to a terminal disclaimer.

(21) Appl. No.: 10/509,331

(22) PCT Filed: Apr. 25, 2003

(86) PCT No.: PCT/EP03/04335

§ 371 (c)(1),
(2), (4) Date: Oct. 7, 2004

(87) PCT Pub. No.: WO03/091192

PCT Pub. Date: Nov. 6, 2003

(65) Prior Publication Data

US 2005/0215452 A1   Sep. 29, 2005

(30) Foreign Application Priority Data

Apr. 26, 2002 (DE) ................................ 102 18 753
Sep. 18, 2002 (DE) ................................ 102 43 363

(51) Int. Cl.
*C11D 1/722* (2006.01)
*C11D 1/72* (2006.01)
*C11D 1/825* (2006.01)
*C11D 3/37* (2006.01)

(52) U.S. Cl. ............... 510/421; 510/342; 510/360; 510/475; 510/505

(58) Field of Classification Search ............... 510/342, 510/360, 421, 475, 505
See application file for complete search history.

(56) References Cited

U.S. PATENT DOCUMENTS

| | | | |
|---|---|---|---|
| 2,508,036 A | 5/1950 | Kosmin | |
| 4,287,370 A | 9/1981 | Harris et al. | |
| 5,158,922 A | 10/1992 | Hinney et al. | |
| 5,340,495 A | 8/1994 | Mulcahy et al. | |
| 5,434,313 A | 7/1995 | Harrison et al. | |
| 6,482,972 B1 * | 11/2002 | Bahrmann et al. | 560/76 |
| 2003/0092587 A1 * | 5/2003 | Gumbel et al. | 510/175 |

FOREIGN PATENT DOCUMENTS

| | | |
|---|---|---|
| DE | 42 37 178 | 5/1994 |
| DE | 101 17 273 | 10/2002 |
| EP | 0 050 228 | 4/1982 |
| EP | 0 616 026 | 9/1994 |
| EP | 0 616 028 | 9/1994 |
| EP | 0 620 270 | 10/1994 |
| EP | 0 681 865 | 11/1995 |
| WO | 94/11330 | 5/1994 |
| WO | 94/11331 | 5/1994 |
| WO | WO 94/11331 * | 5/1994 |
| WO | 95/27034 | 10/1995 |
| WO | 98/06312 | 2/1998 |
| WO | 99/16775 | 4/1999 |
| WO | 00/74845 | 12/2000 |
| WO | 01/04183 | 1/2001 |
| WO | 01/32820 | 5/2001 |
| WO | 01/64772 | 9/2001 |

OTHER PUBLICATIONS

Beilstein E IV 1, p. 3268, no date given.
"Aldehydes, Aliphatic and Araliphatic", Ullmanns Encyclopedia of Industrial Chemistry, 5$^{th}$ ed., vol. A1, pp. 323-328, no date given.
Roempp. Chemie Lexikon, 9$^{th}$ ed., p. 91, no date given.
Marcel Guerbert, C.R. Acad. Sci. Paris 128, 511, pp. 1002-1004 1899, no date given.
Veibel, S. et al. "On the Mechanism of the Guerbet Reaction", Tetrahedron, vol. 23, pp. 1723-1733 1967, no month given.
Gee, Geoffrey et al. "The Polymerization of Epoxides. Part III. The Polymerization of Propylene Oxide by Sodium Alkoxides", J. Chem. Soc., pp. 4298-4303 1961, no month given.
Wojtech, V.B. et al. "Zur Darstellung hochmolekularer Polyaethylenoxyde", Makromol. Chem., vol. 66, pp. 180-195 1966, no month given.
Edited by Plesch, P.H. "The Chemistry of Cationic Polymerization", Pergamon Press, New York, pp. 45-94 1963, no month given.
Tai, Louis Ho Tan. "Formulating Detergents and Personal Care Products: A Guide to Product Development", AOCS Press, pp. 209-226 2000, no month given.

* cited by examiner

*Primary Examiner*—Brian Mruk
(74) *Attorney, Agent, or Firm*—Oblon, Spivak, McClelland, Maier & Neustadt, P.C.

(57) ABSTRACT

The alkoxylate mixtures comprise alkoxylates of the formula (I)

$$C_5H_{11}CH(C_3H_7)CH_2O(A)_n(B)_mH \qquad (I)$$

where
A is ethyleneoxy,
B is $C_{3-10}$-alkyleneoxy or mixtures thereof,
where groups A and B may be present in random distribution, alternately or in the form of two or more blocks in any order,
n is a number from 0 to 30,
m is a number from 0 to 20,
n+m is at least 1
where
70 to 99% by weight of alkoxylates A1 in which $C_5H_{11}$ has the meaning n-$C_5H_{11}$, and
1 to 30% by weight of alkoxylates A2 in which $C_5H_{11}$ has the meaning $C_2H_5CH(CH_3)CH_2$ and/or $CH_3CH(CH_3)CH_2CH_2$,
are present in the mixture.

12 Claims, No Drawings

$C_{10}$-ALKANOLALKOXYLATE MIXTURES AND THE USE THEREOF

The present invention relates to the use of $C_{10}$-alkanol alkoxylate mixtures, to $C_{10}$-alkanol alkoxylate mixtures of this type and to processes for their preparation.

Alkoxylates of aliphatic alcohols are used widely as surfactants, emulsifiers or foam-suppressing agents. The wetting and emulsifier properties here depend heavily on the type of alcohol and on the type and amount of the alkoxide adducts.

WO 94/11331 relates to the use of alkoxylates of 2-propylheptanol in detergent compositions for degreasing hard surfaces. The alkoxylates have 2 to 16 alkylene oxide groups. The majority of the alkylene oxide groups is preferably in the form of ethylene oxide. According to the examples, exclusively ethoxylated alcohols are used. It is also described that the alcohols can firstly be reacted with ethylene oxide and then with propylene oxide. However, no examples or properties are given for such alkoxylates. It is stated that the described alkoxylates exhibit good detergency and wetting action, combined with low foaming. Additionally, it is stated that the alkoxylates have a desired thickening effect in formulations.

WO 94/11330 relates to alkoxylates of 2-propylheptanol and to the use thereof. The alkoxylates contain 2-propylheptanol reacted firstly with 1 to 6 mol of propylene oxide and then with 1 to 10 mol of ethylene oxide. According to the examples, a 2-propylheptanol reacted firstly with 4 mol of propylene oxide and then with 6 mol of ethylene oxide is used. It is stated that the alkylene oxide adducts exhibit an improved ratio of foaming behavior to detergency. In addition, it is stated that the alkoxylates exhibit a good wetting behavior. They are used in detergent compositions for cleaning textile materials.

U.S. Pat. No. 2,508,036 relates to the use of 2-n-propylheptanol ethoxylates which contain 5 to 15 mol of ethylene oxide as wetting agents in aqueous solutions. It is described that the products can be used as surfactants in detergents. Processes for the alkoxylation of 2-propylheptanol are known in principle from the prior art. WO 01/04183 describes, for example, a process for the ethoxylation of hydroxyfunctional starter compounds which is carried out in the presence of a double-metal cyanide compound as catalyst.

It is an object of the present invention to provide alkanol alkoxylates which are suitable as emulsifier, foam regulator and as wetting agent for hard surfaces. The alkoxylates should exhibit, in particular, good emulsifying behavior and a low contact angle on hard surfaces upon use. In addition, they should reduce the interfacial tension in liquid systems. The alkoxylates should in general exhibit an advantageous property spectrum when used as emulsifier, foam regulator or as wetting agent. Furthermore, the amount of residual alcohol should be reduced in order to avoid unpleasant odors.

We have found that this object is achieved according to the invention by alkoxylate mixtures comprising alkoxylates of the formula (I)

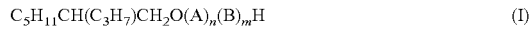

$$C_5H_{11}CH(C_3H_7)CH_2O(A)_n(B)_mH \quad (I)$$

where

A is ethyleneoxy,

B is $C_{3-10}$-alkyleneoxy, preferably propyleneoxy, butyleneoxy, pentyleneoxy or mixtures thereof, where groups A and B may be present in random distribution, alternately or in the form of two or more blocks in any order, n is a number from 0 to 30, m is a number from 0 to 20 n+m is at least 1 where 70 to 99% by weight of alkoxylates A1 in which $C_5H_{11}$ has the meaning n-$C_5H_{11}$, and 1 to 30% by weight of alkoxylates A2 in which $C_5H_{11}$ has the meaning $C_2H_5CH(CH_3)CH_2$ and/or $CH_3CH(CH_3)CH_2CH_2$, are present in the mixture.

We have found that the above alkoxylate mixtures exhibit excellent emulsifier properties and can be used as nonfoaming or low-foaming wetting agents for hard surfaces. The alkoxylates exhibit low contact angles in the case of the wetting of hard surfaces and permit the establishment of low interfacial tensions in liquid systems.

The alkoxylate mixtures of the formula (I) can thus particularly advantageously be used in particular as emulsifier, foam regulator and as wetting agent for hard surfaces in surfactant formulations for cleaning hard surfaces, in humectants, cosmetic, pharmaceutical and crop protection formulations, paints, coating compositions, adhesives, leather degreasing compositions, formulations for the textile industry, fiber processing, metalworking, food industry, water treatment, paper industry, fermentation, mineral processing and in emulsion polymerizations. Further details on the individual fields of use are given below.

In the formula (I), n is preferably a number in the range from 0 to 30, in particular from 3 to 12. m is preferably a number in the range from 0 to 8, in particular 1 to 8, particularly preferably 1 to 5. B is preferably propyleneoxy and/or butyleneoxy.

In the alkoxylates according to the invention, propyleneoxy units can firstly be joined to the alcohol radical, followed by ethyleneoxy units. If n and m have a value greater than 1, then the corresponding alkoxy radicals are preferably in block form. n and m refer here to a mean value, which arises as an average for the alkoxylates. n and m may therefore also deviate from whole-number values. In the alkoxylation of alkanols, a distribution of the degree of alkoxylation is generally obtained, which can be adjusted to a certain extent through the use of different alkoxylation catalysts. In the alkoxylate mixtures according to the invention, it is also possible for ethyleneoxy units to firstly be joined to the alcohol radical, followed by propyleneoxy units. Furthermore, random mixtures of ethylene oxide units and propylene oxide units may be present. 3- or more-block alkoxylation and mixed alkoxylation are also possible. It is also possible that only ethylene oxide units A or only units B, in particular propylene oxide units, are present. Through the choice of suitable amounts of groups A and B, the spectrum of properties of the alkoxylate mixtures according to the invention can be adapted in each case to requirements in practice. Particular preference is given to carrying out the reaction firstly with propylene oxide, butylene oxide, pentene oxide or mixtures thereof and subsequently with ethylene oxide. It is, however, likewise possible for the reaction to take place with ethylene oxide on its own.

Particularly preferably, in the formula (I), B is propyleneoxy. n is then particularly preferably a number from 1 to 20, m is particularly preferably a number from 1 to 8.

The alkoxylate mixtures according to the invention are obtained by alkoxylation of the parent alcohols $C_5H_{11}CH$ ($C_3H_7$)$CH_2OH$. The starting alcohols can be mixed from the individual components, giving rise to the ratio according to the invention. They can be prepared by aldol condensation of valeraldehyde and subsequent hydrogenation. The preparation of valeraldehyde and the corresponding isomers takes place by hydroformylation of butene, as described, for example, in U.S. Pat. No. 4,287,370; Beilstein E IV 1, 32 68, Ullmanns Encyclopedia of Industrial Chemistry, 5th Edition, Volume A1, pages 323 and 328 f. The subsequent aldol condensation is described, for example, in U.S. Pat. No. 5,434,313 and Römpp, Chemie Lexikon, 9th Edition, keyword "Aldol-Addition" page 91. The hydrogenation of the aldol condensation product follows general hydrogenation conditions.

Furthermore, 2-propylheptanol can be prepared by condensation of 1-pentanol (as a mixture of the corresponding 1-methylbutanols) in the presence of KOH at elevated temperatures, see e.g. Marcel Guerbet, C.R. Acad Sci Paris 128, 511, 1002 (1899). Furthermore, reference is made to Römpp, Chemie Lexikon, 9th Edition, Georg Thieme Verlag Stuttgart, and the citations given therein, and also to Tetrahedron, Vol. 23, pages 1723 to 1733.

In the formula (I), the radical $C_5H_{11}$ can have the meaning n-$C_5H_{11}$, $C_2H_5CH(CH_3)CH_2$ or $CH_3CH(CH_3)CH_2CH_2$. The alkoxylates are mixtures where 70 to 99% by weight, preferably 85 to 96% by weight, of alkoxylates A1 are present in which $C_5H_{11}$ has the meaning n-$C_5H_{11}$, and 1 to 30% by weight, preferably 4 to 15% by weight, of alkoxylates A2 in which $C_5H_{11}$ has the meaning $C_2H_5CH(CH_3)CH_2$ and/or $CH_3CH(CH_3)CH_2CH_2$.

The radical $C_3H_7$ preferably has the meaning n-$C_3H_7$.

The alkoxylation is preferably catalyzed by strong bases, which are expediently added in the form of an alkali metal alkoxide, an alkali metal hydroxide or alkaline earth metal hydroxide, usually in an amount of from 0.1 to 1% by weight, based on the amount of alkanol $R^2$—OH (cf. G. Gee et al., J. Chem. Soc. (1961), p. 1345; B. Wojtech, Makromol. Chem. 66, (1966), p. 180).

An acidic catalysis of the addition reaction is also possible. In addition to Bronsted acids, Lewis acids are also suitable, such as, for example, $AlCl_3$ or $BF_3$ dietherate, $BF_3$, $BF_3 \times H_3PO_4$, $SbCl_4 \times 2H_2O$, hydrotalcite (cf. P. H. Plesch, The Chemistry of Cationic Polymerization, Pergamon Press, New York (1963). Double-metal cyanide (DMC) compounds are also suitable as catalyst.

As DMC compounds it is possible in principle to use all suitable compounds known to the person skilled in the art.

DMC compounds suitable as catalyst are described, for example, in WO 99/16775 and DE 10117273. In particular, double-metal cyanide compounds of the general formula I are suitable as catalyst for the alkoxylation:

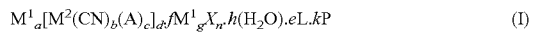

$$M^1{}_a[M^2(CN)_b(A)_c]_d fM^1{}_gX_n \cdot h(H_2O) \cdot eL \cdot kP \qquad (I)$$

in which
- $M^1$ is at least one metal ion, chosen from the group consisting of $Zn^{2+}$, $Fe^{2+}$, $Fe^{3+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{2+}$, $Cr^{3+}$, $Cd^{2+}$, $Hg^{2+}$, $Pd^{2+}$, $Pt^{2+}$, $V^{2+}$, $Mg^{2+}$, $Ca^{2+}$, $Ba^{2+}$, $Cu^{2+}$, $La^{3+}$, $Ce^{3+}$, $Ce^{4+}$, $Eu^{3+}$, $Ti^{3+}$, $Ti^{4+}$, $Ag^+$, $Rh^{2+}$, $Rh^{3+}$, $Ru^{2+}$, $Ru^{3+}$,
- $M^2$ is at least one metal ion, chosen from the group consisting of $Fe^{2+}$, $Fe^{3+}$, $Co^{2+}$, $Co^{3+}$, $Mn^{2+}$, $Mn^{3+}$, $V^{4+}$, $V^{5+}$, $Cr^{2+}$, $Cr^{3+}$, $Rh^{3+}$, $Ru^{2+}$, $Ir^{3+}$,
- A and X, independently of one another, are an anion chosen from the group consisting of halide, hydroxide, sulfate, carbonate, cyanide, thiocyanate, isocyanate, cyanate, carboxylate, oxalate, nitrate, nitrosyl, hydrogensulfate, phosphate, dihydrogenphosphate, hydrogenphosphate or hydrogencarbonate,
- L is a water-miscible ligand chosen from the group consisting of alcohols, aldehydes, ketones, ethers, polyethers, esters, polyesters, polycarbonate, ureas, amides, primary, secondary and tertiary amines, ligands with pyridine nitrogen, nitriles, sulfides, phosphides, phosphites, phosphines, phosphonates and phosphates,
- k is a fraction or integer greater than or equal to zero, and P is an organic additive,
- a, b, c, d, g and n are chosen such that the electron neutrality of the compound (I) is ensured, where c may =0,
- e is the number of ligand molecules, a fraction or integer greater than 0, or 0,
- f and h, independently of one another, are a fraction or integer greater than 0 or 0.

Organic additives P to be mentioned are: polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylamide-co-maleic acid), polyacrylonitrile, polyalkyl acrylates, polyalkyl methacrylates, polyvinyl methyl ether, polyvinyl ethyl ether, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkyleneimines, maleic acid and maleic anhydride copolymers, hydroxyethylcellulose, polyacetates, ionic surface- and interface-active compounds, bile acid or salts thereof, esters or amides, carboxylic esters of polyhydric alcohols and glycosides.

These catalysts can be crystalline or amorphous. Where k is zero, crystalline double-metal cyanide compounds are preferred. Where k is greater than zero, preference is given to crystalline, partially crystalline and also substantially amorphous catalysts.

There are various preferred embodiments of the modified catalysts. A preferred embodiment covers catalysts of the formula (I) in which k is greater than zero. The preferred catalyst then comprises at least one double-metal cyanide compound, at least one organic ligand and at least one organic additive P.

In another preferred embodiment, k is zero, e is optionally also equal to zero and X is exclusively a carboxylate, preferably formate, acetate and propionate. Such catalysts are described in WO 99/16775. In this embodiment, preference is given to crystalline double-metal cyanide catalysts. Also preferred are double-metal cyanide catalysts, as described in WO 00/74845, which are crystalline and plate-like.

The modified catalysts are prepared by combining a metal salt solution with a cyanometallate solution, which may optionally contain both an organic ligand L and also an organic additive P. The organic ligand and optionally the organic additive are then added. In a preferred embodiment of the catalyst preparation, an inactive double-metal cyanide phase is firstly prepared, and this is then converted into an active double-metal cyanide phase by recrystallization, as described in PCT/EP01/01893.

In another preferred embodiment of the catalysts, f, e and k do not equal zero. These are double-metal cyanide catalysts which contain a water-miscible organic ligand (generally in amounts of from 0.5 to 30% by weight) and an organic additive (generally in amounts of from 5 to 80% by weight), as described in WO 98/06312. The catalysts can either be prepared with vigorous stirring (24 000 rpm using Turrax) or with stirring, as described in U.S. Pat. No. 5,158,922.

Catalysts which are particularly suitable for the alkoxylation are double-metal cyanide compounds which contain zinc, cobalt or iron or two of these. For example, Berlin Blue is particularly suitable.

Preference is given to using crystalline DMC compounds. In a preferred embodiment, a crystalline DMC compound of the Zn—Co type which comprises zinc acetate as further metal salt component is used as catalyst. Such compounds crystallize in monoclinic structure and have a plate-like habit. Such compounds are described, for example, in WO 00/74845 or PCT/EP01/01893.

DMC compounds suitable as catalyst can, in principle, be prepared by all methods known to the person skilled in the art. For example, the DMC compounds can be prepared by direct precipitation, "incipient wetness" method, by preparing a precursor phase and subsequent recrystallization.

The DMC compounds can be used as powder, paste or suspension, or be shaped to give a shaped body, be introduced into shaped bodies, foams or the like, or be applied to shaped bodies, foams or the like.

The catalyst concentration used for the alkoxylation, based on the final quantity structure, is typically less than 2 000 ppm (i.e. mg of catalyst per kg of product), preferably less than 1 000 ppm, in particular less than 500 ppm, particularly preferably less than 100 ppm, for example less than 50 ppm or 35 ppm, in particular preferably less than 25 ppm.

The addition reaction is carried out at temperatures of from about 90 to 240° C., preferably from 120 to 180° C., in a closed vessel. The alkylene oxide or the mixture of different alkylene oxides is added to the mixture of alkanol mixture according to the invention and alkali under the vapor pressure of the alkylene oxide mixture which prevails at the chosen reaction temperature. If desired, the alkylene oxide can be diluted by up to about 30 to 60% with an inert gas. This ensures additional safety against explosion-like polyaddition of the alkylene oxide.

If an alkylene oxide mixture is used, then polyether chains are formed in which the various alkylene oxide building blocks are distributed in a virtually random manner. Variations in the distribution of the building blocks along the polyether chain arise on the basis of different reaction rates of the components and can also be achieved voluntarily through the continuous introduction of an alkylene oxide mixture of program-controlled composition. If the different alkylene oxides are reacted one after the other, polyether chains are obtained which have a block-like distribution of the alkylene oxide building blocks.

The length of the polyether chains varies within the reaction product statistically about an average value which essentially corresponds to the stoichiometric value which arises from the amount added.

Preferred alkoxylate mixtures of the formula (I) can be obtained according to the invention by reacting alcohols of the formula $C_5H_{11}CH(C_3H_7)CH_2OH$ firstly with propylene oxide and then with ethylene oxide under alkoxylation conditions or only with ethylene oxide. Suitable alkoxylation conditions are described above and in Nikolaus Schönfeldt, Grenzflächenaktive Äthylenoxid-Addukte [Interface-active ethylene oxide adducts], Wissenschaftliche Verlagsgesellschaft mbH Stuttgart, 1984. The alkoxylation is generally carried out in the presence of basic catalysts such as KOH without a diluent. However, the alkoxylation can also be carried out with the co-use of a solvent. To prepare these alkoxylate mixtures according to the invention, the alcohols are firstly reacted with a suitable amount of propylene oxide and then with a suitable amount of ethylene oxide, or only with ethylene oxide. In the process, a polymerization of the alkylene oxide is set in motion in which a random distribution of homologues inevitably results, the average value of which is given in the present case by n and m.

As a result of the propoxylation preferably carried out first according to the invention and ethoxylation which is only carried out subsequently, it is possible to reduce the content of residual alcohol in the alkoxylates since propylene oxide is added more uniformly to the alcohol component. In contrast thereto, ethylene oxide preferably reacts with ethoxylates, meaning that in the case of an initial use of ethylene oxide for the reaction with the alkanols, both a broad homologue distribution and also a high content of residual alcohol result. The avoidance of relatively large amounts of residual alcohol present in the product is particularly advantageous for odor reasons. The alcohol mixtures used according to the invention generally have an intrinsic odor which can be largely suppressed by complete alkoxylation. Alkoxylates obtained by customary processes often have an intrinsic odor which is undesired for many applications.

Surprisingly, it has been found that this effect occurs even when the amounts of propylene oxide used are small, i.e. in accordance with the invention less than 1.5 equivalents, based on the alcohol used, in particular less than 1.2 equivalents, particularly preferably less than 1 equivalent.

The alkoxylate mixtures according to the invention require only one propylene oxide (PO) block of very short length bonded directly to the alcohol to reduce the residual alcohol content. This is therefore particularly very advantageous as the biodegradability of the product decreases as the PO block is extended. Such alkoxylate mixtures thus permit maximum degrees of freedom in the choice of the length of the PO block, the length downwards being limited by the increasing residual alcohol content, and upwards by the deterioration in the biodegradability. This is then particularly advantageous when only a short ethylene oxide block follows the PO block.

For the purposes of the present invention, it is therefore further preferred that m is an integer or fraction where $0<m\leq5$, for example $0<m\leq2$, preferably $0<m\leq1.5$, particularly preferably $0<m\leq1.2$, in particular $0<m<1$.

According to the invention, it is not necessary for a large residual content of alcohol to be present in the alkoxylate mixtures according to the invention. According to one embodiment of the invention, the alkoxylate mixtures have a reduced alcohol content.

The alkoxylate mixtures according to the invention exhibit improved wetting on hard surfaces.

The advantageous wetting behavior of the mixtures according to the invention can, for example, be determined by measuring the contact angle on glass, polyethylene oxide or steel. The improved wetting behavior leads to better performance in the case, in particular, of rapid cleaning processes. This is surprising since the chain lengthening of the starting alcohol usually diminishes the dynamic and wetting properties. The alkoxylate mixtures according to the invention can thus be used to increase the wetting rate of aqueous formulations. The alkoxylate mixtures according to the invention can thus also be used as solubilizers which, in particular, do not have a negative effect on the wetting ability of wetting auxiliaries even in dilute systems, but have a positive effect. They can be used for increasing the solubility of wetting auxiliaries in aqueous formulations which comprise nonionic surfactants. In particular, they are used for increasing the wetting rate in aqueous wetting agents.

In addition, the alkoxylate mixtures according to the invention are used for reducing interfacial tension, for example in aqueous surfactant formulations. The reduced interfacial tension can be determined, for example, by the pendant drop method. From this also arises a better action of the alkoxylate mixtures according to the invention as emulsifier or coemulsifier. The alkoxylate mixtures according to the invention can also be used for reducing the interfacial tension in short times of, customarily, less than one second or for accelerating the establishment of the interfacial tension in aqueous surfactant formulations.

The present invention likewise provides cleaning, wetting, coating, adhesive, leather degreasing, humectant or textile-treatment compositions or cosmetic, pharmaceutical or crop protection formulations which comprise at least one alkoxylate mixture of the formula (I) as defined above. The compositions preferably comprise 0.1 to 20% by weight of the alkoxylate mixtures. Preferred fields of use for the alkoxylate mixtures according to the invention are described in more detail below.

The alkoxylate mixtures according to the invention are preferably used in the following areas:

Surfactant formulations for cleaning hard surfaces: suitable surfactant formulations to which the alkoxylates according to the invention can be added are described, for example, in Formulating Detergents and Personal Care Products by Louis Ho Tan Tai, AOCS Press, 2000.

They comprise, for example as further components, soaps, anionic surfactants such as LAS or paraffin sulfonates or FAS or FAES, acid, such as phosphoric acid, amidosulfonic acid, citric acid, lactic acid, acetic acid, other organic and inorganic acids, solvents, such as ethylene glycol, isopropanol, complexing agents, such as EDTA, NTA, MGDA, phosphonates, polymers, such as polyacrylates, maleic acid-acrylic acid copolymers, alkali donors, such as hydroxides, silicates, carbonates, perfume oils, oxidizing agents, such as perborates, peracids or trichloroisocyanuric acid, Na or K dichloroisocyanurates, enzymes; see also Milton J. Rosen, Manilal Dahanayake, Industrial Utilization of Surfactants, AOCS Press, 2000 and Nikolaus Schönfeldt, Grenzflächenaktive Ethylenoxidaddukte [Interface-active ethylene oxide adducts]. These also in principle cover formulations for the other said applications. These may be household cleaners, such as all-purpose cleaners, dishwashing detergents for manual and automatic dishwashing, metal degreasing, industrial applications such as cleaners for the food industry, bottle washing, etc. They may also be printing roll and printing plate cleaning compositions in the printing industry. Suitable further ingredients are known to the person skilled in the art.

Humectants, in particular for the printing industry.

Cosmetic, pharmaceutical and crop protection formulations. Suitable crop protection formulations are described, for example, in EP-A-0 050 228. Further ingredients customary for crop protection compositions may also be present.

Paints, coating compositions, inks, pigment preparations and adhesives in the coating and polymer film industry.

Leather degreasing compositions.

Formulations for the textile industry, such as leveling agents or formulations for yarn cleaning.

Fiber processing and auxiliaries for the paper and pulp industry.

Metal processing, such as metal refining and electroplating sector.

Food industry.

Water treatment and drinking water production.

Fermentation.

Mineral processing and dust control.

Building auxiliaries.

Emulsion polymerization and preparation of dispersions.

Coolants and lubricants.

Such formulations usually comprise ingredients such as surfactants, builders, fragrances and dyes, complexing agents, polymers and other ingredients. Typical formulations are described, for example, in WO 01/32820. Further ingredients suitable for different applications are described in EP-A-0 620 270, WO 95/27034, EP-A-0 681 865, EP-A-0 616 026, EP-A-0 616 028, DE-A42 37 178 and U.S. Pat. No. 5,340,495 and in Schönfeldt, see above, by way of example.

In general, the alkoxylate mixtures according to the invention can be used in all fields where the action of interface-active substances is necessary.

The structures according to the invention have low aquatoxicity and good biodegradability compared to known structures, meaning that they are advantageously suitable for a large number of fields of application.

The present invention is described in more detail below by reference to examples.

EXAMPLES

Preparation Example 1

DMC Catalyst 16 000 g of aqueous hexacyanocobaltic acid (cobalt content: 9 g/l) were introduced into a stirred-tank reactor with a volume of 30 l, fitted with propeller stirrer, submerged tube for metered addition, pH probe and scattered light probe, and heated to 50° C. with stirring. Then, with stirring at a stirrer speed of 0.4 W/l, 9 224 g of aqueous zinc acetate dihydrate solution (zinc content: 2.6% by weight), which was likewise heated to 50° C., were introduced over the course of 15 minutes.

351 g of Pluronic® PE 6200 (BASF AG) were added to this precipitation suspension, and the mixture was stirred for a further 10 minutes.

A further 3 690 g of aqueous zinc acetate dihydrate solution (zinc content: 2.6% by weight) were then metered in with stirring at a stirring energy of 1 W/l over the course of 5 minutes.

The suspension was after-stirred for two hours. During this time, the pH dropped from 4.02 to 3.27 and then remained constant. The precipitation suspension obtained in this way was then filtered off and washed on the filter with 6 times the cake volume of water.

The moist filter cake was dried and dispersed in Tridekanol® N using a gap rotor mill. The resulting suspension had a multimetal cyanide content of 5% by weight.

Example 1

2-propylheptanol+5 EO, 25 ppm of DMC 474 g (3.0 mol) of 2-propyl-1-heptanol (isomer mixture of 87% 2-propyl-1-heptanol, 11% 2-propyl-4-methyl-1-hexanol, <1% 2-propyl-5-methyl-1-hexanol) and 0.567 g of 5% strength suspension of double-metal cyanide in 2-propylheptanol isomer mixture (25 ppm based on the product) as catalyst were dehydrated at a temperature of 80° C. and about 1 mbar, then placed in a 2 l pressurized autoclave, flushed three times with nitrogen and then heated to 120° C. After the temperature had been reached, 660 g (15 mol) of ethylene oxide were continuously metered in over 1.05 hours at a pressure of from 0.1 to 3.7 bar (pressure ramp 6 bar/90 min). Following the addition of all of the oxide, the mixture was left to react until the pressure was constant (20 minutes), then cooled to 80° C., flushed three times with nitrogen and emptied. The resulting product was degassed at 80° C. on a rotary evaporator under reduced pressure (<30 mbar) (reaction product not filtered).

Example 2

2-propylheptanol+3 EO, 25 ppm of DMC

The reaction was carried out analogously to example 1 with 474 g (3.0 mol) of 2-propylheptanol isomer mixture, 0.44 g of double-metal cyanide suspension and 397 g (9.0 mol) of ethylene oxide.

Example 3

2-propylheptanol+8 EO, 25 ppm of DMC

The reaction was carried out analogously to example 1 with 474 g (3.0 mol) of 2-propylheptanol isomer mixture, 0.77 g of double-metal cyanide suspension and 1 060 g (24.0 mol) of ethylene oxide.

Preparation Example 2

Synthesis of Ethoxylates of 2-propylheptanol by Means of KOH Catalysis

2-Propylheptanol and KOH (finely powdered) were mixed and dehydrated at 80° C. and 40 mbar for 1 hour. The reaction product was introduced into an autoclave, the autoclave was rendered inert twice with nitrogen and then heated to 120° C. Over the course of 15 minutes, ethylene oxide was metered in to a maximum pressure of 1 bar. The system was maintained for 5 min at this pressure, then the pressure was increased to 3 bar by adding ethylene oxide over the course of 60 min, the system was held at this pressure for 5 hours, and finally the pressure was increased to 6 bar. During the last metered addition, ethylene oxide was added only until the desired amount of ethylene oxide was reached. The pressure was then maintained at 6 bar through the metered addition of nitrogen. After a reaction time of a further 10 hours, the system was left to cool to 80° C., and the reaction product was discharged. Volatile components were removed on a rotary evaporator at 30 mbar and 80° C.

Example 4

2-propylheptanol+3 EO, KOH Catalyzed

The synthesis was carried out analogously to preparation example 2.474 g of 2-propylheptanol (3.0 mol), 397 g of ethylene oxide (9.0 mol) and 1.8 g of KOH were used.

a) The starting alcohol used was pure 2-PH, prepared by distillation of the technical-grade mixture with a purity greater than 99%. The product has the following properties:

Wetting on textile surfaces (EN 1772): 13 sec (23° C., 1 g/l in 2 g of soda/l)

Foaming ability (EN 12728): about 20 ml (40° C.; 2 g/l; 1.8 mmol of $Ca^{2+}$ ions, after 30 sec)

Surface tension (DIN 53914): about 26.8 mN/m (1 g/l; 23° C.)

Degree of ethoxylation acc. to OH number: 3.1 mol of EO b) The starting alcohol used was 2-propylheptanol, technical-grade quality with about 90% of 2-Ph and about 10% of 4-methyl-2-propylhexanol. The product has the following properties:

Wetting on textile surfaces (EN 1772): 12 sec (23° C., 1 g/l in 2 g of soda/l)

Foaming ability (EN 12728): about 20 ml (40° C.; 2 g/l; 1.8 mmol of $Ca^{2+}$ ions, after 30 sec)

Surface tension (DIN 53914): about 27.2 mN/m (1 g/l; 23° C.)

Degree of ethoxylation acc. to OH number: 2.8 mol of EO

Example 5

2-propylheptanol+5 EO, KOH Catalyzed

The synthesis was carried out analogously to preparation example 2.474 g of 2-propylheptanol (3.0 mol), 661 g of ethylene oxide (15.0 mol) and 2.3 g of KOH were used.

a) The starting alcohol used was pure 2-PH, prepared by distillation of the technical-grade mixture with a purity greater than 99%. The product has the following properties:

Wetting on textile surfaces (EN 1772): 10 sec (23° C., 1 g/l in 2 g of soda/l)

Foaming ability (EN 12728): 25 ml (40° C.; 2 g/l; 1.8 mmol of $Ca^{2+}$ ions, after 30 sec)

Surface tension (DIN 53914): about 27.1 mN/m (1 g/l; 23° C.)

Degree of ethoxylation acc. to OH number: 5.2 mol of EO b) The starting alcohol used was 2-propylheptanol, technical-grade quality with about 90% of 2-Ph and about 10% of 4-methyl-2-propylhexanol. The product has the following properties:

Wetting on textile surfaces (EN 1772): 9 sec (23° C., 1 g/l in 2 g of soda/l)

Foaming ability (EN 12728): 30 ml (40° C.; 2 g/l; 1.8 mmol of $Ca^{2+}$ ions, after 30 sec)

Surface tension (DIN 53914): about 26.3 mN/m (1 g/l; 23° C.)

Degree of ethoxylation acc. to OH number: 4.6 mol of EO

Example 6

2-propylheptanol+7 EO, KOH Catalyzed

The synthesis was carried out analogously to preparation example 2.474 g of 2-propylheptanol (3.0 mol), 925 g of ethylene oxide (21.0 mol) and 2.8 g of KOH were used.

a) The starting alcohol used was pure 2-PH, prepared by distillation of the technical-grade mixture with a purity greater than 99%. The product has the following properties:

Wetting on textile surfaces (EN 1772): 14 sec (23° C., 1 g/l in 2 g of soda/l)

Foaming ability (EN 12728): 330 ml (40° C.; 2 g/l; 1.8 mmol of $Ca^{2+}$ ions, after 30 sec)

Surface tension (DIN 53914): about 27.8 mN/m (1 g/l; 23° C.)

Degree of ethoxylation acc. to OH number: 7.4 mol of EO b) The starting alcohol used was 2-propylheptanol, technical-grade quality with about 90% of 2-Ph and about 10% of 4-methyl-2-propylhexanol. The product has the following properties:

Wetting on textile surfaces (EN 1772): 13 sec (23° C., 1 g/l in 2 g of soda/l)

Foaming ability (EN 12728): 350 ml (40° C.; 2 g/l; 1.8 mmol of $Ca^{2+}$ ions, after 30 sec)

Surface tension (DIN 53914): about 27.1 mN/m (1 g/l; 23° C.)

Degree of ethoxylation acc. to OH number: 7.1 mol of EO

Example 7

2-propylheptanol+10 EO, KOH Catalyzed

The synthesis was carried out analogously to preparation example 2.474 g of 2-propylheptanol (3.0 mol), 1 322 g of ethylene oxide (30.0 mol) and 3.6 g of KOH were used.

a) The starting alcohol used was pure 2-PH, prepared by distillation of the technical-grade mixture with a purity greater than 99%. The product has the following properties:

Wetting on textile surfaces (EN 1772): 47 sec (23° C., 1 g/l in 2 g of soda/l)

Foaming ability (EN 12728): 380 ml (40° C.; 2 g/l; 1.8 mmol of $Ca^{2+}$ ions, after 30 sec)

Surface tension (DIN 53914): 30.5 mN/m (1 g/l; 23° C.)

Degree of ethoxylation acc. to OH number: 10.4 mol of EO b) The starting alcohol used was 2-propylheptanol, technical-grade quality with about 90% of 2-Ph and about 10% of 4-methyl-2-propylhexanol. The product has the following properties:

Wetting on textile surfaces (EN 1772): 40 sec (23° C., 1 g/l in 2 g of soda/l)

Foaming ability (EN 12728): 370 ml (40° C.; 2 g/l; 1.8 mmol of $Ca^{2+}$ ions, after 30 sec)

Surface tension (DIN 53914): about 30.7 mN/m (1 g/l; 23° C.)

Degree of ethoxylation acc. to OH number: 10.2 mol of EO

The physicochemical properties and tests for wetting, foam etc. thus exhibit comparable performance irrespective of whether the preparation was carried out using a technical grade or isomerically pure grade.

Example 8

Alkoxylation with EO with DMC Catalyst 8.1 2-Propylheptanol+3 EO 316 g (2.0 mol) of 2-propyl-1-heptanol (isomer mixture of 87% 2-propyl-1-heptanol, 11% 2-propyl-4-methyl-1-hexanol, <1% of 2-propyl-5-methyl-1-hexanol) and 35 ppm of double-metal cyanide catalyst (based on the product) were dehydrated at a temperature of 100° C. and about 20 mbar for 2 hours in a pressurized autoclave. The mixture was then flushed three times with nitrogen and heated to 140° C. After the temperature has been reached, a total of 264 g (6.0 mol) of ethylene oxide were metered in with stirring. When the ethylene oxide metered addition was complete, the mixture was stirred for a further 1 h at 140° C., and the reactor was flushed three times with nitrogen, then evacuated to degas to 20 mbar, then cooled to 80° C., and emptied. The reaction product was not filtered.

Residual alcohol content (2-propyl-1-heptanol): 9.6%

8.2 2-Propylheptanol+4 EO

The procedure was as in example 8.1. However, 8.0 mol of ethylene oxide instead of 6.0 mol were added.

Residual alcohol content (2-propyl-1-heptanol): 5.8%

8.3 2-Propylheptanol+5 EO

The procedure was as in example 8.1. However, 10.0 mol of ethylene oxide instead of 6.0 mol were added.

Residual alcohol content (2-propyl-1-heptanol): 2.7%

8.4 2-Propylheptanol+6 EO

The procedure was as in example 8.1. However, 12.0 mol of ethylene oxide instead of 6.0 mol were added.

Residual alcohol content (2-propyl-1-heptanol): 1.4%

8.5 2-Propylheptanol+7 EO

The procedure was as in example 8.1. However, 14.0 mol of ethylene oxide instead of 6.0 mol were added.

Residual alcohol content (2-propyl-1-heptanol): 0.8%

8.6 2-Propylheptanol+8 EO

The procedure was as in example 8.1. However, 16.0 mol of ethylene oxide instead of 6.0 mol were added.

Residual alcohol content (2-propyl-1-heptanol): 0.3%

8.7 2-Propylheptanol+10 EO

The procedure was as in example 8.1. However, 20.0 mol of ethylene oxide instead of 6.0 mol were added.

Residual alcohol content (2-propyl-1-heptanol): 0.2%

8.8 2-Propylheptanol+14 EO

The procedure was as in example 8.1. However, 28.0 mol of ethylene oxide instead of 6.0 mol were added.

Residual alcohol content (2-propyl-1-heptanol): 0.1%

Example 9

Alkoxylation with PO with DMC Catalyst 9.1 2-Propylheptanol+0.8 PO 316 g (2.0 mol) of 2-propyl-1-heptanol (isomer mixture of 87% 2-propyl-1-heptanol, 11% of 2-propyl-4-methyl-1-hexanol, <1% of 2-propyl-5-methyl-1-hexanol) and 35 ppm of double-metal cyanide catalyst (based on the product) were dehydrated at a temperature of 100° C. and about 20 mbar for two hours in a pressurized autoclave. The system was then flushed three times with nitrogen and then heated to 140° C. After the temperature had been reached, a total of 93 g (1.6 mol) of propylene oxide were metered in at 140° C. with stirring. When the PO metered addition was complete, the mixture was stirred for a further 15 minutes at 140° C., and the reactor was flushed three times with nitrogen, then evacuated to degas to 20 mbar, then cooled to 80° C., and emptied.

Residual alcohol content (2-propyl-1-heptanol): 28.6%

9.2 2-Propylheptanol+1.0 PO

The procedure was as in example 9.1. However, 2.0 mol of propylene oxide instead of 1.6 mol were added, and the process was carried out at a reaction temperature of 140° C.

Residual alcohol content (2-propyl-1-heptanol): 24.2%

9.3 2-Propylheptanol+1.20 PO

The procedure was as in example 9.1. However, 2.4 mol of propylene oxide instead of 1.6 mol were added, and the process was carried out at a reaction temperature of 160° C.

Residual alcohol content (2-propyl-1-heptanol): 20.0%

9.4 2-Propylheptanol+1.20 PO

The procedure was as in example 9.1. However, 2.4 mol of propylene oxide instead of 1.6 mol were added, and the process was carried out at a reaction temperature of 140° C. Residual alcohol content (2-propyl-1-heptanol): 19.8%

9.5 2-Propylheptanol+1.23 PO

The procedure was as in example 9.1. However, 2.46 mol of propylene oxide instead of 1.6 mol were added, and the process was carried out at a reaction temperature of 120° C. Residual alcohol content (2-propyl-1-heptanol): 20.8%

9.6 2-Propylheptanol+1.28 PO

The procedure was as in example 9.1. However, 2.56 mol of propylene oxide instead of 1.6 mol were added, and the process was carried out at a reaction temperature of 140° C. Residual alcohol content (2-propyl-1-heptanol): 17.7%

9.7 2-Propylheptanol+1.30 PO

The procedure was as in example 9.1. However, 2.6 mol of propylene oxide instead of 1.6 mol were added, and the process was carried out at a reaction temperature of 140° C. Residual alcohol content (2-propyl-1-heptanol): 17.6%

9.8 2-Propylheptanol+1.40 PO

The procedure was as in example 9.1. However, 2.8 mol of propylene oxide instead of 1.6 mol were added, and the process was carried out at a reaction temperature of 140° C. Residual alcohol content (2-propyl-1-heptanol): 15.8%

9.9 2-Propylheptanol+1.44 PO

The procedure was as in example 9.1. However, 2.88 mol of propylene oxide instead of 1.6 mol were added, and the process was carried out at a reaction temperature of 140° C. Residual alcohol content (2-propyl-1-heptanol): 14.8%

9.10 2-Propylheptanol+1.51 PO

The procedure was as in example 9.1. However, 3.02 mol of propylene oxide instead of 1.6 mol were added, and the process was carried out at a reaction temperature of 120° C. Residual alcohol content (2-propyl-1-heptanol): 15.0%

9.11 2-Propylheptanol+1.63 PO

The procedure was as in example 9.1. However, 3.26 mol of propylene oxide instead of 1.6 mol were added, and the process was carried out at a reaction temperature of 160° C. Residual alcohol content (2-propyl-1-heptanol): 10.1%

9.12 2-Propylheptanol+1.71 PO

The procedure was as in example 9.1. However, 3.42 mol of propylene oxide instead of 1.6 mol were added, and the process was carried out at a reaction temperature of 120° C. Residual alcohol content (2-propyl-1-heptanol): 10.7%

Example 10

Alkoxylation with PO and EO with DMC Catalyst 10.1 2-Propylheptanol+0.8 PO+3 EO 316 g (2.0 mol) of 2-propyl-1-heptanol (isomer mixture of 87% 2-propyl-1-heptanol, 11% of 2-propyl-4-methyl-1-hexanol, <1% of 2-propyl-5-methyl-1-hexanol) and 35 ppm of double-metal cyanide catalyst (based on the product) were dehydrated at a temperature of 100° C. and about 20 mbar for two hours in a pressurized autoclave. The system was then flushed three times with nitrogen and then heated to 140° C. After the temperature had been reached, a total of 93 g (1.6 mol) of propylene oxide were metered in at 140° C. with stirring. When the PO metered addition was complete, the mixture was stirred for a further 15 minutes at 140° C., and then the metered addition of a total of 264 g (6.0 mol) of ethylene oxide was started. When the ethylene oxide metered addition was complete, the mixture was stirred for a further 1 h at 140° C., and the reactor was flushed three times with nitrogen, then evacuated to degas to 20 mbar, then cooled to 80° C., and emptied. The reaction product was not filtered.

Residual alcohol content (2-propyl-1-heptanol): 1.9%

10.2 2-Propylheptanol+1.0 PO+3 EO

The procedure was as in example 10.1. However, 2.0 mol of propylene oxide and 6.0 mol of ethylene oxide were added.

Residual alcohol content (2-propyl-1-heptanol): 1.3%

10.3 2-Propylheptanol+1.2 PO+3 EO

The procedure was as in example 10.1. However, 2.4 mol of propylene oxide and 6.0 mol of ethylene oxide were added.

Residual alcohol content (2-propyl-1-heptanol): 0.9%

10.4 2-Propylheptanol+0.8 PO+4 EO

The procedure was as in example 10.1. However, 1.6 mol of propylene oxide and 8.0 mol of ethylene oxide were added.

Residual alcohol content (2-propyl-1-heptanol): 1.0%

10.5 2-Propylheptanol+1.0 PO+4 EO

The procedure was as in example 10.1. However, 2.0 mol of propylene oxide and 8.0 mol of ethylene oxide were added.

Residual alcohol content (2-propyl-1-heptanol): 0.7%

10.6 2-Propylheptanol+1.3 PO+4 EO

The procedure was as in example 10.1. However, 2.6 mol of propylene oxide and 8.0 mol of ethylene oxide were added.

Residual alcohol content (2-propyl-1-heptanol): 0.5%

10.7 2-Propylheptanol+0.6 PO+5 EO

The procedure was as in example 10.1. However, 1.2 mol of propylene oxide and 10.0 mol of ethylene oxide were added.

Residual alcohol content (2-propyl-1-heptanol): 0.8%

10.8 2-Propylheptanol+1.2 PO+5 EO

The procedure was as in example 10.1. However, 2.4 mol of propylene oxide and 10.0 mol of ethylene oxide were added.

Residual alcohol content (2-propyl-1-heptanol): 0.14%

10.9 2-Propylheptanol+1.0 PO+6 EO

The procedure was as in example 10.1. However, 2.0 mol of propylene oxide and 12.0 mol of ethylene oxide were added.

Residual alcohol content (2-propyl-1-heptanol): 0.12%

10.10 2-Propylheptanol+1.2 PO+6 EO

The procedure was as in example 10.1. However, 2.4 mol of propylene oxide and 12.0 mol of ethylene oxide were added.

Residual alcohol content (2-propyl-1-heptanol): 0.09%

10.11 2-Propylheptanol+1.3 PO+6 EO

The procedure was as in example 10.1. However, 2.6 mol of propylene oxide and 12.0 mol of ethylene oxide were added.

Residual alcohol content (2-propyl-1-heptanol): 0.06%

10.12 2-Propylheptanol+1.2 PO+7 EO

The procedure was as in example 10.1. However, 2.4 mol of propylene oxide and 14.0 mol of ethylene oxide were added.
Residual alcohol content (2-propyl-1-heptanol): 0.03%

10.13 2-Propylheptanol+1.3 PO+8 EO

The procedure was as in example 10.1. However, 2.6 mol of propylene oxide and 16.0 mol of ethylene oxide were added.
Residual alcohol content (2-propyl-1-heptanol): 0.02%

10.14 2-Propylheptanol+1.0 PO+10 EO

The procedure was as in example 10.1. However, 2.0 mol of propylene oxide and 20.0 mol of ethylene oxide were added.
Residual alcohol content (2-propyl-1-heptanol): 0.01%

10.15 2-Propylheptanol+1.0 PO+14 EO

The procedure was as in example 10.1. However, 2.0 mol of propylene oxide and 28.0 mol of ethylene oxide were added.
Residual alcohol content (2-propyl-1-heptanol): 0.01%

A comparison of the values for the residual alcohol content of a product containing PO and EO determined arithmetically in each case from example 8 and 9 with the values obtained experimentally for example 10 clearly shows that the initial propoxylation and subsequent ethoxylation leads to a significantly reduced residual alcohol content compared to the theoretically expected value.

We claim:

1. A mixture comprising alkoxylates of the formula (I)

$$C_5H_{11}CH(C_3H_7)CH_2O(A)_n(B)_mH \quad (I)$$

wherein the mixture comprises
85% to 96% by weight of alkoxylats A1 wherein $C_5H_{11}$ is n-$C_5H_{11}$, and
4% to 15% by weight of alkoxylates A2 wherein $C_5H_{11}$ is $C_2H_5CH(CH_3)CH_2$ and/or $CH_3CH(CH_3)CH_2CH_2$, wherein
A is ethyleneoxy,
B is $C_{3-10}$-alkyleneoxy or mixtures thereof,
where groups A and B may be present in random distribution, alternately or in the form of two or more blocks in any order,
n is a number from 0 to 30,
m is a number from 1 to 8, and
wherein the $C_{3-10}$-akyleneoxy or mixtures thereof is firstly added to the $C_5H_{11}CH(C_3H_7)CH_2O$-radical.

2. The mixture as claimed in claim 1, wherein $C_3H_7$ is n-$C_3H_7$.

3. The mixture as claimed in claim 1, wherein B is propyleneoxy, and n is a number from 1 to 20.

4. A process for preparing the mixture as claimed in claim 1, the process comprising:
reacting an alcohol mixture with $C_{2-5}$-alkylene oxides under alkoxylation conditions, optionally in the presence of a double-metal cyanide compound as catalyst.

5. A method of preparing a product, the method comprising:
combining the mixture of claim 1 with at least one substance to create the product,
wherein the at least one substance is selected from the group consisting of a soap, an anionic surfactant, an organic acid, an inorganic acid, a solvent, a complexing agent, a polymer, a copolymer, an alkali donor, a perfume oil, an oxidizing agent, an enzyme, and combinations thereof, and
wherein the product is an emulsifier, a foam regulator or a wetting agent for hard surfaces.

6. The method as claimed in claim 5, wherein the product is a detergent, a surfactant formulation for the cleaning of hard surfaces, a humectant, a cosmetic formulation, a pharmaceutical formulation, a crop protection formulation, a paint, a coating composition, an adhesive, a leather degreasing composition, a formulation for the textile industry, fiber processing, metal working, food industry, water treatment, paper industry, fermentation or mineral processing or a product to be comprised in emulsion polymerizations.

7. A washing, cleaning, wetting, coating, adhesive, leather degreasing, humectant or textile-treatment composition or cosmetic, pharmaceutical or crop protection formulation comprising the mixture as claimed in claim 1.

8. The mixture as claimed in claim 2, wherein B is propyleneoxy, and n is a number from 1 to 20.

9. A process for the preparation of the mixture as claimed in claim 2, the process comprising:
reacting an alcohol mixture with $C_{2-5}$-alkylene oxides under alkoxylation conditions, optionally in the presence of a double-metal cyanide compound as catalyst.

10. A process for the preparation of the mixture as claimed in claim 3, the process comprising:
reacting the alcohol mixture with $C_{2-5}$-alkylene oxides under alkoxylation conditions, optionally in the presence of a double-metal cyanide compound catalyst.

11. A washing, cleaning, wetting, coating, adhesive, leather degreasing, humectant or textile-treatment composition or cosmetic, pharmaceutical or crop protection formulation comprising the mixture as claimed in claim 2.

12. A washing, cleaning, wetting, coating, adhesive, leather degreasing, humectant or textile-treatment composition or cosmetic, pharmaceutical or crop protection formulation comprising the mixture as claimed in claim 3.

* * * * *